(12) United States Patent
Millen

(10) Patent No.: US 7,678,060 B1
(45) Date of Patent: Mar. 16, 2010

(54) METHOD OF MONITORING A STATE OF HEALTH, AND A WELLNESS/EMOTIONAL STATE MONITOR IMPLEMENTING THE METHOD

(76) Inventor: Ernest W. Millen, 390 Rivers Ridge Cir., Newport News, VA (US) 23608

( * ) Notice: Subject to any disclaimer, the term of this patent is extended or adjusted under 35 U.S.C. 154(b) by 0 days.

(21) Appl. No.: 12/074,769

(22) Filed: Mar. 6, 2008

Related U.S. Application Data

(60) Provisional application No. 60/905,694, filed on Mar. 8, 2007.

(51) Int. Cl.
*A61B 5/02* (2006.01)

(52) U.S. Cl. ............... 600/504; 600/483; 600/485; 600/500; 600/526

(58) Field of Classification Search ............ 600/483, 600/485, 490, 500–504, 526
See application file for complete search history.

(56) References Cited

U.S. PATENT DOCUMENTS

| | | | |
|---|---|---|---|
| 4,625,277 A | 11/1986 | Pearce et al. | |
| 5,101,828 A | 4/1992 | Welkowitz et al. | |
| 5,178,154 A * | 1/1993 | Ackmann et al. | 600/526 |
| 5,289,823 A | 3/1994 | Eckerle | |
| 5,507,291 A | 4/1996 | Stirbl et al. | |
| 5,535,753 A * | 7/1996 | Petrucelli et al. | 600/485 |
| 5,692,501 A * | 12/1997 | Minturn | 600/301 |
| 6,203,495 B1 * | 3/2001 | Bardy | 600/301 |
| 6,340,346 B1 | 1/2002 | Almog et al. | |
| 6,478,735 B1 | 11/2002 | Pope et al. | |
| 6,730,039 B2 * | 5/2004 | Nakagawa | 600/485 |
| 6,819,950 B2 | 11/2004 | Mills | |
| 7,192,403 B2 * | 3/2007 | Russell | 600/504 |
| 7,249,603 B2 | 7/2007 | El-Nokaly et al. | |
| 7,306,563 B2 | 12/2007 | Huang | |
| 2003/0065270 A1 * | 4/2003 | Raines et al. | 600/504 |
| 2003/0176788 A1 | 9/2003 | Crutchfield et al. | |
| 2003/0204144 A1 | 10/2003 | Lin | |
| 2004/0111014 A1 | 6/2004 | Hickle | |
| 2004/0152956 A1 | 8/2004 | Korman | |
| 2005/0004479 A1 * | 1/2005 | Townsend et al. | 600/500 |
| 2005/0261593 A1 * | 11/2005 | Zhang et al. | 600/485 |

\* cited by examiner

*Primary Examiner*—Robert L Nasser
*Assistant Examiner*—Michael D'Angelo
(74) *Attorney, Agent, or Firm*—Kimberly A. Chasteen

(57) ABSTRACT

A method of deriving a single integer figure of merit representative of vital signs of a mammalian, generally a human subject. A systolic blood pressure S, a diastolic pressure D, and a heart rate PR are used to calculate an Inferred Blood Flow (IBF) using the equation IBF=(S−D)* PR/C where C is a constant, typically 100. A procedure is provided for establishing a statistically valid baseline IBF number against which subsequent IBF readings may be compared to assess the wellness (physiological and emotional) of the subject relative to medical community limits and standards. A self-contained apparatus for making measurements, and computing and storing an IBF is also provided. A normalized single digit scale, the Millen Scale is provided and ideal for use with the present invention. A system for monitoring wellness and/or emotional state of being using the IBF parameter is also provided.

5 Claims, 5 Drawing Sheets

Figure 1

Name _____ Contact _____

Date: _____ Time: _____

| Min: | : | : | : | : | : | : | : | ○ Placid Vital Signs & Low IBF | Pbar and s, (S-D)bar & s, IFBbar & s+ |
|---|---|---|---|---|---|---|---|---|---|
| 1 Meausrement | Setup | 1 | 2 | 3 | 4 | 5 | 6 | 7 | |
| 2 Systolic | | | | | | | | | |
| 3 Diastolic | | | | | | | | | |
| 4 Pulse | | | | | | | | | ±  |
| 5 SD | | | | | | | | | ± |
| 6 IBF | | | | | | | | | ± |
| 7 | | | | | | | | IBFbar/Low IBF = | Stab: s = |
| 8 Observations | : | : | : | : | : | : | : | | |

Date: _____ Time: _____

| Min: | : | : | : | : | : | : | : | ○ Placid Vital Signs & Low IBF | Pbar and s, (S-D)bar & s, IFBbar & s+ |
|---|---|---|---|---|---|---|---|---|---|
| 1 Meausrement | Setup | 1 | 2 | 3 | 4 | 5 | 6 | 7 | |
| 2 Systolic | | | | | | | | | |
| 3 Diastolic | | | | | | | | | |
| 4 Pulse | | | | | | | | | ± |
| 5 SD | | | | | | | | | ± |
| 6 IBF | | | | | | | | | ± |
| 7 | | | | | | | | IBFbar/Low IBF = | Stab: s = |
| 8 Observations | : | : | : | : | : | : | : | | |

*Figure 2*

METHOD OF MONITORING A STATE OF HEALTH, AND A WELLNESS/EMOTIONAL STATE MONITOR IMPLEMENTING THE METHOD

RELATED APPLICATIONS

This application is based in part on, and claims priority to U.S. Provisional Patent Application Ser. No. 60/905,964 titled INFERRED BLOOD FLOW AND WELLNESS MONITOR METHOD, filed Mar. 8, 2007, which is included herein in its entirety by reference.

FIELD OF THE INVENTION

The invention pertains to measuring a physiological parameter of a person and, more particularly, to a method of determining an inferred blood flow parameter in a human subject, and a wellness/emotional state monitor based upon a statistical analysis of the inferred blood flow parameter.

BACKGROUND OF THE INVENTION

Both the medical community and informed laity are well aware of the variability in blood pressure measurements. Medical professionals are familiar with the many causes for such variations. These causes include a person's physical condition, a person's mental state subject to many outside influences, the quality of the measuring equipment, the competency of data interpreters, and the naturally variable response to normal bodily functions. Despite these numerous variables, healthcare providers of all types and levels of experience typically make important health decisions based upon non-scientific data and evaluations (e.g., a single or small number of blood pressure measurements). According to well-known scientific data processing methodology, using such a single measurement "tradition" introduces a high risk for error. It is difficult to estimate the damage that this traditional procedure may have inflicted upon humans due to inaccurate information and mis-diagnosis.

DISCUSSION OF THE RELATED ART

Numerous attempts have been made to eliminate the aforementioned problems associated with blood pressure measurements, particularly to monitor wellness, to reduce stress, and to predict behavior based on factors such as blood pressure, etc. For example, U.S. Pat. No. 4,625,277 for BLOOD PRESSURE MEASURING DEVICE HAVING ADAPTIVE CUFF DEFLATION RATE, issued Nov. 25, 1986 to Christopher Pearce et al., discloses a cuff wherein the deflation rate is determined from an algorithm based upon previous blood pressure measurements.

U.S. Pat. No. 5,101,828 for METHODS AND APPARATUS FOR NONINVASIVE MONITORING OF DYNAMIC CARDIAC PERFORMANCE, issued Apr. 7, 1992 to Walter Welkowitz et al., shows noninvasive monitoring of cardiac performance to determine a blood flow parameter.

U.S. Pat. No. 5,289,823 for NON-INVASIVE AORTIC BLOOD FLOW SENSOR AND METHOD FOR NON-INVASIVELY MEASURING AORTIC BLOOD FLOW, issued Mar. 1, 1994 to Joseph S. Eckerle, shows a non-invasive blood flow measuring system to monitor cardiac output in real time.

U.S. Pat. No. 5,507,291 for METHOD AND AN ASSOCIATED APPARATUS FOR REMOTELY DETERMINING INFORMATION AS TO PERSON'S EMOTIONAL STATE, issued Apr. 16, 1996 to Robert C. Stirbl et al., teaches the remote determination of a person's emotional state. The method includes a step of deriving a rate of blood flow.

U.S. Pat. No. 6,340,346 for METHOD AND SYSTEM FOR SYSTEM IDENTIFICATION OF PHYSIOLOGICAL SYSTEMS, issued Jan. 22, 2002 to Yael Almog et al., teaches a system for monitoring a pregnancy, wherein elements include blood flow and the emotional state of the mother to determine a vector asserted to represent the physiological state of the mother.

U.S. Pat. No. 6,478,735 for PHYSIOLOGICAL FEEDBACK METHOD AND SYSTEM, issued Nov. 12, 2002 to Alan T. Pope et al., discloses a system of physiological feedback relating overall emotional and/or physical sensation to a monitored physiological effect. The system utilizes a blood flow measurement.

U.S. Pat. No. 6,819,950 for METHOD FOR NONINVASIVE CONTINUOUS DETERMINATION OF PHYSIOLOGIC CHARACTERISTICS, issued Nov. 16, 2004 to Alexander K. Mills, provides a method for noninvasive determination of physiologic characteristics, which relies in part on monitoring blood flow and blood pressures. MILLS identifies heart rate and blood pressure as common indices of wellness. A blood flow formula is also presented.

U.S. Pat. No. 7,192,403 for METHODS, APPARATUS AND ARTICLES-OF-MANUFACTURE FOR NONINVASIVE MEASUREMENT AND MONITORING OF PERIPHERAL BLOOD FLOW, PERFUSION, CARDIAC OUTPUT BIOPHYSICS STRESS AND CARDIOVASCULAR CONDITION, issued Mar. 20, 2007 to Ted W. Russell, shows a noninvasive method of estimating blood flow.

U.S. Pat. No. 7,249,603 for METHOD FOR MEASURING ACUTE STRESS IN A MAMMAL, issued Jul. 31, 2007 to Magda El-Nokaly et al., teaches a method for measuring stress, relying in part on blood flow.

U.S. Pat. No. 7,306,563 for PULSE DIAGNOSTIC SYSTEM, issued Dec. 11, 2007 to Herb E. Huang, discloses a pulse-based diagnostic system intended to diagnose illness and health of a patient.

United States Published Patent Application No. 2003/0176788 for DETECTING, ASSESSING, AND DIAGNOSING SLEEP APNEA, published Sep. 18, 2003, upon application by Kevin E. Crutchfield et al., uses among other things blood flow data in a sleep apnea diagnosis system.

United States Published Patent Application No. 2003/0204144 for SPHYGMORGH MEASURE METHOD AND DEVICE FOR PULSE RATE PRESSURE AND BLOOD FLOW RATE, published Oct. 30, 2003, upon application by Chin-Yuh Lin, provides a formula for determining blood flow.

United States Published Patent Application No. 2004/0111014 for SYSTEM AND METHOD FOR PROVIDING SENSOR FUSION, published Jun. 10, 2004, upon application by Randall S. Hickle, also provides a formula for determining blood flow.

United States Published Patent Application No. 2004/0152956 for PHYSIOLOGICAL MONITORING SYSTEM FOR A COMPUTATIONAL DEVICE OF A HUMAN SUBJECT, published Aug. 5, 2004, upon application by Ronen Korman, teaches a system which uses, for example, blood flow to derive medical parameters which can be manipulated to construct an automated diagnosis of a patient's health.

None of the patents or published patent applications, taken singly, or in any combination are seen to teach or suggest the novel features of the method and system of the present invention.

SUMMARY OF THE INVENTION

In accordance with the present invention, there is provided a method for calculating an Inferred Blood Flow (IBF), a unitless figure of merit useful as both a wellness monitor and as a measure of emotional intensity. IBF is computed using the formula:

$$(BP_s - BP_d) * PR / C \text{ where:}$$

$BP_s$—Systolic blood pressure;
$BP_d$—Diastolic blood pressure;
PR—Heart pulse rate; and
C—a constant, typically 100.

A baseline IBF may be compared to an instant IBF and any deviation therefrom can be evaluated. Deviations among IBF tend to be much smaller than deviations among, for example, traditional blood pressure measurements. Consequently, a departure from a baseline state of wellness may readily be noted without the problems of false positives so often present when comparing raw blood pressure readings or other similar vital signs.

In addition, a deviation in IBF from baseline IBF may correlate with the emotional state of a subject. In other words, the IBF may measure the intensity and stability (i.e., variability) of a subject's emotional state. Consequently, real-time IBF values may be used to predict, for example, disruptive behavior caused by an agitated emotional state of a subject, for example, in a prison, mental hospital, or under some other stressful circumstance.

The novel algorithm may be embodied in a portable monitoring apparatus, optionally equipped with a telemetry feature for such real-time monitoring of one or more subjects.

It is, therefore, an object of the invention to provide an algorithm for calculating an Inferred Blood Flow (IBF).

It is another object of the invention to provide an apparatus for receiving and monitoring systolic and diastolic blood pressures and calculating an IBF therefrom.

It is an additional object of the invention to provide an apparatus wherein baseline IBF values for one or more subjects may be stored and compared to an instant IBF acquired and computed by the apparatus.

It is a further object of the invention to provide an apparatus for use as a wellness monitor based upon comparison of an instant IBF to a stored, baseline IBF.

It is a still further object of the invention to provide an apparatus for monitoring the IBF of a subject in real-time and for providing the IBF information to a monitor remotely located therefrom via a telemetry link.

BRIEF DESCRIPTION OF THE DRAWINGS

Various objects, features, and attendant advantages of the present invention will become more fully appreciated as the same becomes better understood when considered in conjunction with the accompanying drawings, in which like reference characters designate the same or similar parts throughout the several views, and wherein:

FIG. 1 is a sample data sheet for recording measurements in accordance with the invention;

FIG. 2 is a time history form useful for recording historical data and calculations in accordance with the invention;

DETAILED DESCRIPTION OF THE PREFERRED EMBODIMENT

Figure 3:
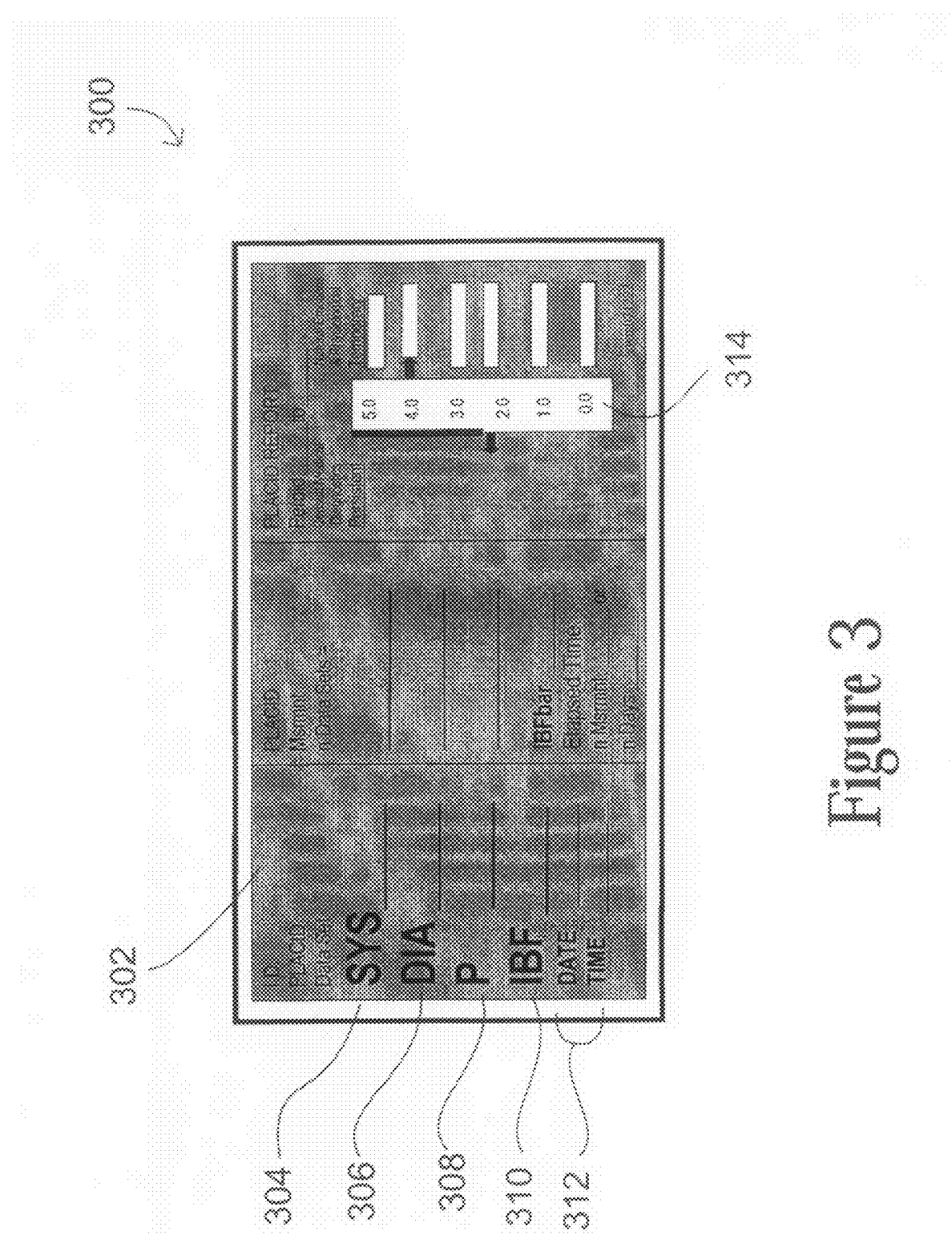
FIG. 3 is a schematic representation of a display portion of a first embodiment of a wellness meter in accordance with the with the present invention.

The present invention provides a novel algorithm for determining Inferred Blood Flow (IBF), a unitless number useful for both monitoring the wellness of a subject and for measuring the intensity and variability of an emotion of a subject.

Scientific Vital Signs Information (SVSI) (i.e., traditional blood pressure parameters and complementing physiological blood flow information) provides one clinical diagnostic means allowing health care professionals to track wellness of their patients. However, traditionally, only health care professionals with appropriate credentials were able to successfully interpret SVSI for diagnostic purposes.

The novel IBF is calculated by the formula:

$$IBF = (BP_s - BP_d) * PR / C \text{ where:}$$

$BP_s$—Systolic blood pressure;
$BP_d$—Diastolic blood pressure;
PR—Heart pulse rate; and
C—a constant, typically 100.

Using the IBF number in accordance with the present invention may allow persons other than highly trained medical professionals to interpret data obtained, for example, from a blood pressure monitor incorporating an IBF calculator and indicator. Such devices may effectively become "wellness monitors" rather than merely devices for obtaining raw blood pressure and pulse rate data. Such wellness monitors, when used with the novel scientific standard data analysis protocols described herein, screen out momentarily high measurement values taken placid at rest that may be due to natural influences.

The wellness monitoring process of the invention is based on the novel IBF figure of merit as well as a percentage change in blood flow (% cBF) parameter. The resulting novel value of placid, at-rest state of blood flow is the consequence of, and is determined by iterated data sets and statistical analyses, wherein the placid value is determined by the lowest value reading that is followed by two higher ones. Changing blood flow (% cBF), which is the difference between a baseline IBF and an instant IBF value, is an important indicator of change in a state of wellness. The % cBF parameter is driven by the interaction of the $BP_s$, $BP_d$, and PR parameters.

Understudying the variable nature of each SVSI parameter ($BP_s$, $BP_d$, $BP_s - BP_d$, PR, and IBF) measurement and calculation is important. The heart/blood system may, of course, momentarily respond to natural mental and physiological causes with traditional hyper-level values. Such hyper-values, then, may not be a symptom of disease. Hyper-level data may also be caused by equipment or human error during the measurement process.

Any single blood pressure measurement may be in the traditional hyper-level range during a natural event without a consequent significant change in the blood flow. Sometimes as the result of a natural influence, only the systolic pressure will change. Under other circumstances, only the diastolic pressure will change. However, it is believed that diastolic pressure seems to be an "anchor" event in that it is less effected by the aforementioned measurement factors.

Sometimes only $BP_s$–$BP_d$ or only PR, the heart pulse rate, will change due to some influence, such as a new medication being taken by a subject. The heart adjusts the interactions of the parameters in order to accommodate the blood flow needs demanded by a host of normal mind/body functions. Tracking the blood flow with replicated measurements or dynamic monitoring helps to interpret the changes in $BP_s$, $BP_s$–$BP_d$, and $BP_d$ parameters to determine if any are transient or persistent, the latter possibly indicating a disease.

The persistence of traditional hyper-level blood pressure data consistent with persistent increased blood flow is a primary indicator of abnormality (disease or accident). In addition to tracking heart parameter variation, only diagnostic physicians should assess whether hyper-values are truly disease or incident indications by also considering a host of other possible causes. Possible causes to be considered in reaching a correct diagnosis may include the patient's immediate medical/medicine history, clinical history (e.g., laboratory analysis, etc.), environmental conditions/exposures, physiological conditions, mental state, etc.

Some examples of natural causes for momentary at-rest hyper-blood pressure measurements include:

(1) movement of the patient's body (e.g., physical movements, moans, coughs, belches, etc.) during a measurement;

(2) disturbed senses (e.g., unusual feelings, sights, smells, sounds, itches, pain, need to flatulate, need to use a rest room, etc.);

(3) mental activity (anything other than neutral with mind "disengaged," or placid at rest); and (4) white coat syndrome (i.e., blood pressure increase caused by anxiety of the patient in the examination room or in the presence of medical personnel).

Traditional hyper-level blood pressure measurements with such causes generally do not persist. They can be eliminated as indications of disease by scientifically-based statistical protocols involving replicated measurements. A single traditional hyper-blood pressure measurement performed non-scientifically does not indicate a disease. Some types of mental diseases and emotional disturbances may also cause momentary traditional hyper-changes in vital signs data, but most diseases, generally do not momentarily come and go. A good example is a fever caused by an infection. Temperatures due to an infection do not momentarily come and go.

Persistence in deviations from established norms when diagnosing is a concept believed to be well-known to the medical community. Therefore, a single blood pressure measurement for diagnostic purposes, in view of its naturally variable nature, may not be considered a statistically significant (i.e., "scientific") measurement, yet single measurements are believed to be widely relied upon in practice. Competent strategies exist that can overcome the traditional idea that one, or even two, blood pressure measurements are sufficient for a competent diagnosis.

Recently developed blood pressure monitors in the prior art provide three or more averaged blood pressure measurements. In addition, the averaged measurement(s) may be printed and/or graphed. These features acknowledge the single measurement problem and provide tools that help more scientifically measure blood pressure. The question that must be asked is whether such simple averaging is a sufficient solution. Generally accepted statistical methodology suggests it does not. The method of the present invention, however, provides a scientific, statistical protocol requiring more data replications across a greater period of time. It is believed that the additional time required pays ample rewards in improved accuracy of measurements and the minimization of mis-diagnosis relative to measurement procedures of the prior art.

Physiologically, variations in blood pressure measurements can occur naturally due to the causes discussed hereinabove. Such variations can be dynamic, over very short time intervals (e.g., intervals measured in seconds). Such intervals may be much smaller than the time it takes to obtain a blood pressure measurement. A scientific determination of a person's blood pressure, therefore, requires a number of measurements designed to overcome or resolve the dynamics relative to the persistence of any one of the intending single parameters being hyper or abnormal.

Blood flow is essential to biological functions, and information about blood flow changes, whether dynamic or persistent, is important for the competent diagnosis of disease. The blood flow parameter commonly provided in operating rooms during surgical procedures is typically dynamically measured. Operating room equipment, which provides dynamic blood flow measurements, is typically expensive and therefore, not available to most diagnosticians. Vascular physicians may use a portable Doppler blood flow checker to validate dynamic flow. The replicated Inferred Blood Flow (IBF) parameter of the inventive method provides a dynamic indication of flow changes over time. Significantly, the calculation of IBF requires no additional equipment; it utilizes the traditional, easily measured $BP_S$, $BP_d$, and PR parameters and is derived by a simple calculation defined by well-known physical laws.

It has been determined that the most useful (i.e., the parameter with the highest confidence and least risk for misdiagnosis) blood pressure related parameter is the IBF values that are associated with a person who is placid at-rest. IBF value is derived from a number of measurements taken over time. This is accomplished by five to seven Scientific Vital Signs (SVS) measurement sets following a preliminary measurement set that may identify correctable variables.

Several relationships have been experimentally verified. First, significant and sustained variations in any of $BP_s$, $BP_d$, $BP_s$–$BP_d$, IBF, and PR persisting dynamically in traditional hyper-ranges may suggest the existence of a health problem. Also, natural changes in blood pressure parameters and pulse, even though momentarily in the traditional hyper-range, may not be persistent placid at-rest, nor interactively effect the natural range of IBF at rest. Hyper or hypo $BP_S$, $BP_d$ values may occur, but the relative amount of blood per heartbeat may not change. Finally, high or low $BP_s$–$BP_d$ values may occur, and either the IBF may not change or the pulse may adjust.

The amount of blood flow measured with respect to time that is essential to maintain body operation at rest, and the relative dynamic contributions of $BP_s$, $BP_d$, and PR, causing flow variances, are critical to a scientific understanding of physiological health and vital to the diagnostic process thereof. Abnormal blood flow can occur during hyper, natural, or low blood pressures. The IBF of the present invention can help in the understanding of these dynamic interactions.

While the novel IBF is qualitative and is a unitless figure of merit, the measured data associated therewith may, nonetheless, be transferred into quantitative diagnostics by percentage changes in blood flow compared to baseline IBF values. A dynamic protocol for using the IBF parameter should help diagnosticians quickly identify health issues.

The novel process of the present invention requires a baseline, placid at rest IBF. A typical baseline data set may be obtained in a number of ways. One possible method is described hereinbelow. However, it will be recognized that many other satisfactory data gathering methods may be known to those of skill in the art, and the invention is not considered limited to the method described for purposes of disclosure.

When measuring blood pressure, patient position is important. A highly desirable position is where the patient is prone with his/her arms relaxed and positioned by the sides of the torso. Alternate positions exist, including, for example, sitting with both feet on the floor, a first arm positioned in the lap with the opposite arm supported substantially horizontally (i.e., level) for the attachment of the blood pressure measuring device. Whatever the position, it is important that the patient's entire body be relaxed.

The measuring device, generally an inflatable blood pressure cuff, should be loosely positioned on the patient's arm, typically with a one-finger gap between the inner surface of the cuff and the patient's skin.

The patient's mouth should be free of food or drink (including gum) and the voice box should be inactive.

Prior to commencing measurements, the patient should take several (six is recommended) deep breaths. The breath count should be incremented at exhalation. The sphygmomanometer should next be operated in accordance with the manufacturer's instructions or other standard operating procedure.

During and between blood pressure measurements, the patient should refrain from speaking, eating, drinking, or performing bodily movements of any kind.

Any measurement during which the patient exhibits any physical or mental interruption, for example, sneezing, coughing, or reacting to any environmental distraction, should be discarded.

During and between measurements, the patient should maintain a constant breathing rate, counting at the exhale. Counting helps to maintain a neutral mindset and helps avoid spurious mental diversions.

After making an initial setup measurement, five to seven sets of $BP_S$, $BP_d$, and PR (pulse rate) measurements should be taken and recorded. Upon completion of each measurement set, the resulting IBF for the set is calculated according to the inventive formula: $(BP_s-BP_d)* PR/100$. Note, a constant value of 100 is chosen for purposes of disclosure. It will be recognized that other constant values may be substituted to meet a particular operating circumstance or environment.

The set-up measurement set is ignored. The number of measurement sets to be taken is determined by reviewing the calculated IBF for each of the first five measurement sets. If the lowest observed IBF value occurs in any of measurement sets one, two, or three, five measurement sets is sufficient. If, however, the lowest IBF value is found in set four, a sixth measurement set is required. If the lowest IBF value is found in measurement set five, the seventh measurement set is also required. In other words, the measurement process may be terminated when the lowest calculated IBF is succeeded by two additional higher IBF values.

The arithmetic mean and standard deviation (i.e., x and σ) is calculated for all the $BP_s$, $BP_d$, and PR values of the measurement sets.

Data may be verified by performing additional calculations. First the arithmetic mean is calculated for all $BP_s$, $BP_d$, PR, and IBF values. A mean IBF is calculated from mean values using the formula:

$$\overline{IBF}=(\overline{BP_s}-\overline{BP_d})*\overline{PR}/100.$$

$\overline{IBF}$ should equal the arithmetic mean of the calculated IBF of the measurement sets. If a significant difference is noted, the measurements should be repeated.

Figure 1:
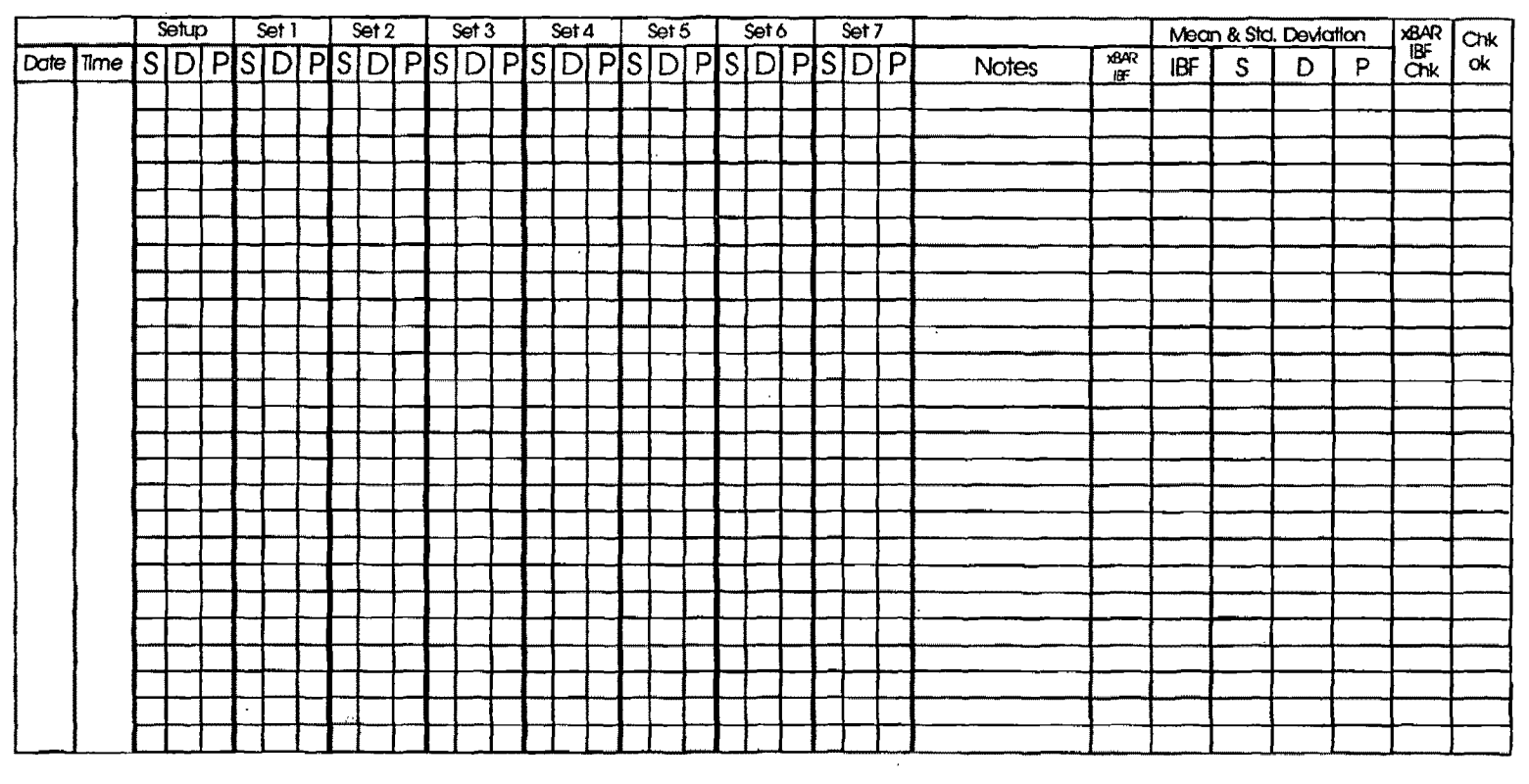

FIGS. 1 and 2 provide sample data sheets and time history forms useful for recording data and calculations for the above-described measurement procedure.

The changing characteristics of blood pressure measurements and blood flow are analogous to ocean tide changes. Ocean tides change within a range, naturally, due primarily to the relative positions of the sun, earth, and moon. The extreme limits of the range are constructed statistically (standard deviations) from accumulated measured data, including routine winds/storms. Abnormal values due to hurricanes, typhoons, and earthquakes, etc. generally are compared with the arithmetic mean tide.

Similarly, rare, unnaturally high/low blood pressures and abnormal blood flows due to accidents/diseases should be discernible, statistically, from the natural ranges of blood pressures and blood flows. Diagnostic practices should screen blood pressures in blood flow data statistically for values that exceed natural data.

A quick glance at a weather close (wind) vane provides information about the wind. The longer the vane is observed, the higher the confidence in the wind direction and its variability. A longer period of observation also allows for a more confident determination of whether the directional changes are gusty or long period. In a similar manner, a single blood pressure measurement provides only a glimpse of a general health condition. Scientifically, it is crude. As with the weathervane, a longer (statistical) look is needed for confidence in the observation. The IBF of the present invention provides such a scientific approach to analyzing performance of the heart and circulatory system of a subject.

The method of the present invention is useful as a wellness (physiological, emotional, or mental) monitor. Once baseline IBF data is obtained, more IBF data sets are taken across a significant span of time, for example, several hours or days. Such data sets, which represent measurements during a variety of time and activities in the life of the monitored subject, may be compared to the baseline data to accurately assess the wellness of the subject. The IBF data gathered may be statistically analyzed to determine the presence and persistence of any deviation compared to the baseline data to indicate an overall "wellness" of the subject. To simplify the interpretation of such a statistical analysis, a single-digit wellness scale (i.e., the Millen Scale, named for the inventor of the method and apparatus of the present invention) is proposed.

A Millen scale number is derived by dividing the placid at-rest IBF by 1800. A simple calculation shows that a 2.0 on the Millen scale corresponds to a traditional upper limit of normal vital signs established by the National Institute of Health (NIH), specifically a blood pressure of 140/90 and a pulse rate of 60-90 beats per minute.

Figure 4:
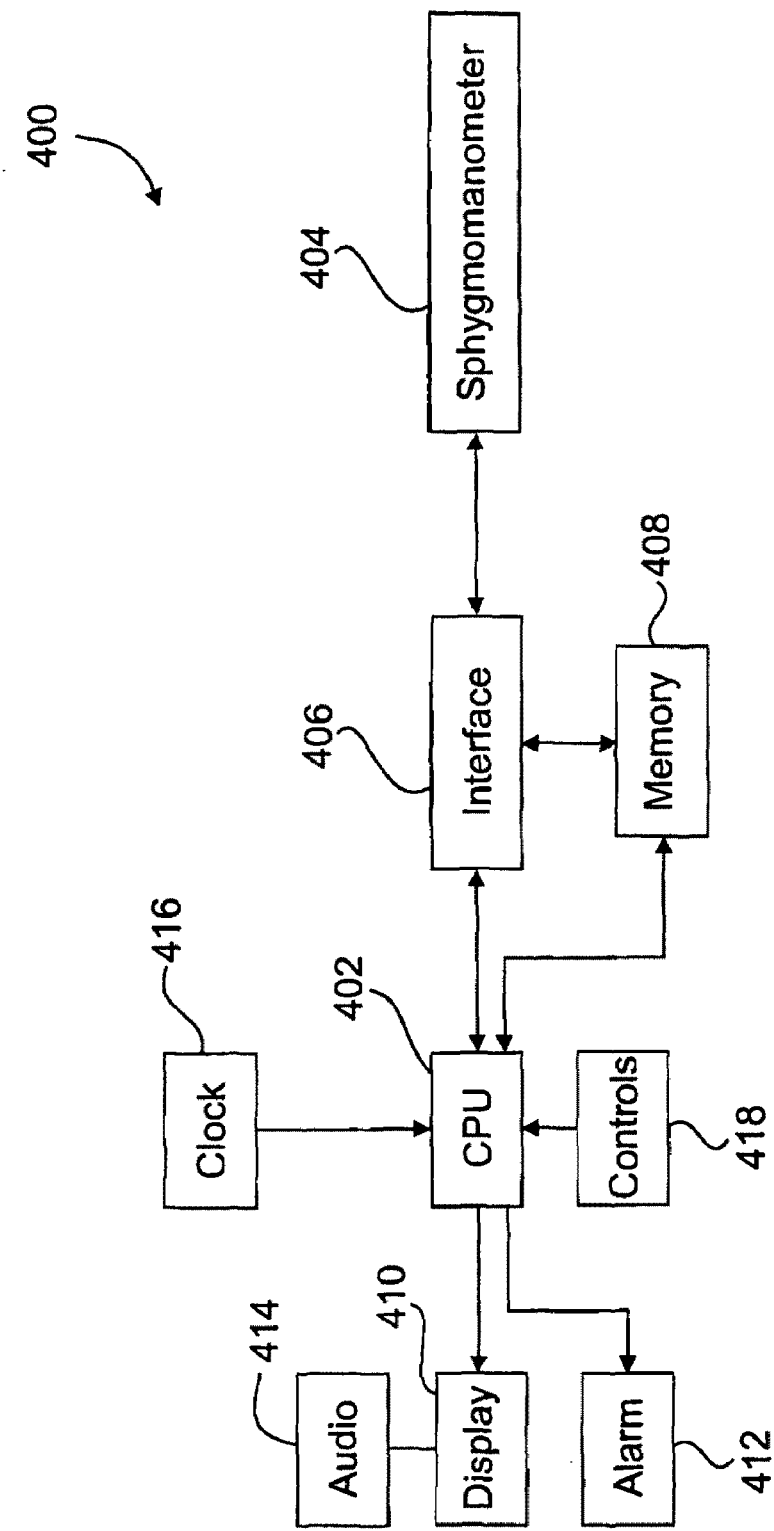
FIG. 4 is a simplified block diagram of the wellness meter of FIG. 3.

A wellness meter, which can measure, calculate, and store data in a compact, easy-to-use package, having a display, implements the IBF method of the invention. Referring now to FIGS. 3 and 4, there is shown a schematic representation of a user interface and a simplified functional block diagram, respectively, of a first embodiment of a wellness meter of the present invention, generally at reference numbers 300 and 400, respectively.

Display 300 has at least a screen region 302. Prominent on screen 302 are SYS(tolic), DIA(stoloic), P(ulse rate), and IBF display regions 304, 306, 308, and 310, respectively. The Millen Scale display 314 is provided. Other fields, none specifically identified, are also provided on display 302. It will be recognized that fields may be added or deleted as necessary to meet a particular operating circumstance or environment.

A CPU 402 provides all computational and control functions of wellness meter 300. CPU 402 may be a microcontroller or any other suitable microprocessor as is well known to those of skill in the art.

A sphygmomanometer 404 is connected to CPU 402 through a control interface 406.

A memory is connected both to CPU 402 and interface 406.

A display 410, and optional alarm 412, are also shown connected to CPU 402. Display 410 and/or alarm 412 my include an audio response unit 414 for verbal annunciation of user instructions and/or test results.

A calendar/clock 416 is connected to CPU 402.

Controls 418 are connected to CPU 402. Controls 418 represent any set of control devices required to take measurements, display test results, and display historic data. Such controls are believed to be well known to those of skill in the art and are not described in further detail herein.

Figure 5:
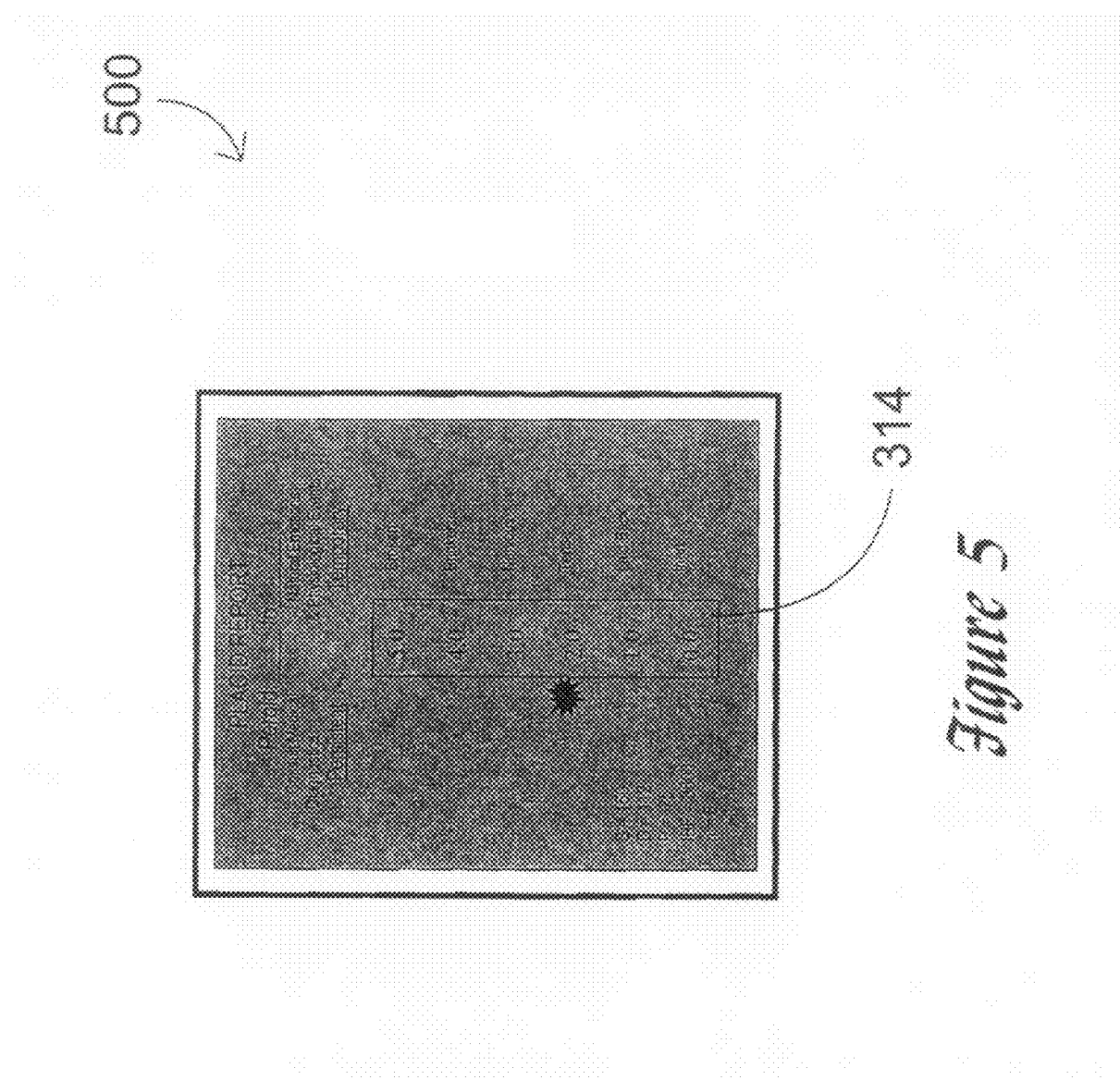
FIG. 5 is a schematic representation of a display portion of an alternate embodiment of a wellness meter in accordance with the present invention.

Referring now to FIG. 5, there is shown a schematic view of a screen of an alternate embodiment of wellness meter 300 (FIG. 3), generally at reference number 500. Wellness meter 500 is a simplified version of wellness meter 300 and shows Millen Scale 314 but few other values.

It has been observed that the single-digit Millen value may correspond to the physical and emotional state of the subject. Consequently, an IBF reading, when compared to baseline (i.e., placid at rest) data, may be useful to determine if a subject is in an unusual emotional state.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. A method for monitoring wellness of a human subject, the steps comprising:
    a. Using at least one selected from the group: computer, processor, and microprocessor, gathering baseline IBF data comprising at least two statistically processed IBF values obtained from a subject placid at rest, each IBF value being calculated by measuring a systolic blood pressure (S), a corresponding diastolic blood pressure (D), and a heart pulse rate (PR), and then calculating said IBF values using the equation: $IBF=(S-D)*PR/C$ where C is a constant, said gathering baseline data step comprising the sub-steps:
        i. Making an initial setup blood pressure measurement;
        ii. After said making an initial setup measurement sub-step (i), making five measurements, each of said five measurements being spaced apart by a time interval;
        iii. Calculating an IBF for each of said five measurements;
        iv. If a lowest one of said calculated IBFs occurs in one of the first three of said five measurements, stopping the measurement process and proceeding to obtaining step (b); and
        v. Otherwise, repeating said making measurements sub-step (iii) until the lowest one of a calculated IBF is followed by at least two higher calculated IBFs
    b. Thereafter, obtaining at least one subsequent IBF value by measuring a systolic pressure (S), a corresponding diastolic blood pressure (D), and a heart pulse rate (PR) of said subject, and then calculating said subsequent IBF value using the equation:

$IBF=(S-D)*PR/C$ where C c. Comparing said at least one subsequent IBF value to said baseline IBF data; and
    d. Drawing a conclusion regarding the wellness of said subject based upon a result of said comparing step (C).

2. The method for monitoring wellness of a human subject recited in claim 1, wherein said constant C is approximately equal to 100.

3. The method for monitoring wellness of a human subject recited in claim 1, the steps further comprising:
    e) dividing each of said baseline IBF data and said at least one subsequent IBF value by a second constant to obtain a single-digit value.

4. The method for monitoring wellness of a human subject recited in claim 3, wherein said dividing step (e) comprises dividing by 1800, whereby a Millen Scale value is obtained.

5. The method for monitoring wellness of a human subject recited in claim 1, the steps further comprising:
    e) using a dedicated apparatus adapted to perform at least one of said obtaining step (b) and said comparing step (c).

* * * * *